(12) United States Patent
Maroto

(10) Patent No.: US 7,593,817 B2
(45) Date of Patent: Sep. 22, 2009

(54) CALCULATING CONFIDENCE LEVELS FOR PEPTIDE AND PROTEIN IDENTIFICATION

(75) Inventor: Fernando M. Maroto, Palo Alto, CA (US)

(73) Assignee: Thermo Finnigan LLC, San Jose, CA (US)

( * ) Notice: Subject to any disclaimer, the term of this patent is extended or adjusted under 35 U.S.C. 154(b) by 913 days.

(21) Appl. No.: 10/738,667

(22) Filed: Dec. 16, 2003

(65) Prior Publication Data

US 2005/0131647 A1 Jun. 16, 2005

(51) Int. Cl.
*G06F 19/00* (2006.01)
*G11C 17/00* (2006.01)
*B01D 59/44* (2006.01)

(52) U.S. Cl. .............................. 702/19; 365/94; 250/282

(58) Field of Classification Search ........................ None
See application file for complete search history.

(56) References Cited

U.S. PATENT DOCUMENTS

| | | |
|---|---|---|
| 6,329,146 B1 | 12/2001 | Crooke et al. |
| 2003/0065451 A1 | 4/2003 | Pineda et al. |
| 2003/0068831 A1 | 4/2003 | Edwards et al. |
| 2003/0158671 A1 | 8/2003 | Gajiwala |

OTHER PUBLICATIONS

Eriksson et al. A model of random mass-matching and its use for automated significance testing in mass specrtometric proteome analysis. Proteomics vol. 2, pp. 262-270 (2002).*

Altschul et al. Gapped BLAST and PSI-BLAST: a new generation of proetin database search programs. Nucleic Acids Research vol. 25, pp. 3389-3402 (1997).*

Roger E. Moore, et al., "Qscore: An Algorithm for Evaluating SEQUEST Database Search Results," *J. Am. Soc. Mass Spectrom* (2002) 13:378-386.

Andrej Shevchenko, et al., "Linking genome and proteome by mass spectrometry: Large-scale identification of yeast proteins from two dimensional gels," *Proc. Natl. Acad. Sci. USA* (1996) 93:14440-14445.

John R. Yates III, "Database searching using mass spectrometry data," *Electrophoresis* (1998) 19: 893-900.

John R. Yates III, "Mass Spectrometry and the Age of the Proteome," *Journal of Mass Spectrometry* (1998) 33:1-19.

David L. Tabb, et al., "Similarity among Tandem Mass Spectra from Proteomic Experiments: Detection, Significance, and Utility," *Analytical Chemistry* (2003) 75:2470-2477.

Jimmy K. Eng, et al., "An Approach to Correlate Tandem Mass Spectral Data of Peptides with Amino Acid Sequences in a Protein Database," *American Society for Mass Spectrometry* (1994) 5:976-989.

Proteomics Core Sequest, Proteomics Core, University of Arizona College of Pharmacy (2002), available at http://web.archive.org/web/20030107062038/http://swehsc.pharmacy.arizona.edu/analysis.

* cited by examiner

*Primary Examiner*—John S Brusca
(74) *Attorney, Agent, or Firm*—Michael C. Staggs; Sharon Upham; Fish & Richardson P.C.

(57) ABSTRACT

Computer programs and methods for defining a misidentification probability for an experimental protein divisible into experimental peptides. The invention receives data representing a set of matches of experimental peptides to reference peptides that can be derived from a protein in a database of proteins; calculates a probability of observing by chance, in a search of the database of proteins, a set of matches equivalent to or better than the represented set of matches; and defines the misidentification probability using the probability of observing by chance a set of matches equivalent to or better than the represented set of matches.

68 Claims, 6 Drawing Sheets

| Sample Peptide | 1st Best Match | 2nd Best Match | ... | 10th Best Match |
|---|---|---|---|---|
| I | protein 1, peptide 2 | protein 2, peptide 1 | | |
| II | protein 1, peptide 3 | | | |
| ... | | | | |
| III | protein 2, peptide 2 | protein 3, peptide 2 | | |

FIG. 4A

| Protein | Peptide | Sample Peptide | X-value | Position |
|---|---|---|---|---|
| | | | | |
| 1 | 2 | I | 0.90 | 1 |
| 1 | 3 | II | 0.36 | 1 |
| 2 | 1 | I | 0.88 | 2 |
| 2 | 2 | III | 0.94 | 1 |
| 3 | 2 | III | 0.40 | 2 |

CALCULATING CONFIDENCE LEVELS FOR PEPTIDE AND PROTEIN IDENTIFICATION

TECHNICAL FIELD

The invention relates to the identification of proteins.

BACKGROUND

Protein identification is a necessary step in many aspects of biological and medical research. The development of large protein databases has made it possible to identify many otherwise unidentified proteins by comparing information from their analysis, such as their sequences or mass spectra, with information in or from the database. Developments in high-throughput peptide analysis techniques, such as robotic gel band excision and digestion, and matrix-assisted laser desorption/ionization (MALDI) mass spectrometry, have made it possible to collect large volumes of data that characterize large numbers of experimental proteins. Such information can be compared with information in databases of known proteins in order to identify such experimental proteins.

A particularly powerful tool for characterizing and identifying proteins is mass spectrometry (MS), especially when used in conjunction with liquid chromatography (LC). With the use of LC/MS, the peptides of proteins that have been proteolytically digested are separated using methods of LC. A mass spectrometer then sorts the peptides according to their relative mass-to-charge ratio (m/z), producing a characteristic spectrum of peaks for the protein. With the use of tandem mass spectrometry (MS/MS), a single peptide of a protein can be selected and subjected to collision-induced dissociation (CID). CID produces fragment ions that are sorted according to their mass-to-charge ratios, producing a characteristic spectrum for the selected peptide. The repeated application of liquid chromatography tandem mass spectrometry (LC-MS/MS) can produce a number of spectra, each characterizing a different peptide.

A protein that has been characterized by methods such as LC-MS/MS can be identified by comparing its experimental data such as the mass spectra of its peptides with characteristic data such as theoretical mass spectra for peptides of previously identified ("known") proteins. By comparing the experimental data of an unknown peptide to theoretically derived properties of known peptide sequences, the unknown peptide as well as the unknown protein to which the unknown peptide belongs can be identified. Searchable protein databases are available, e.g., at the National Center for Biotechnology Information (NCBI) website ncbi.nlm.nih.gov. They include databases of nucleotide sequence information and amino acid sequence information for proteins.

To evaluate MS/MS data for peptides using a nucleotide or protein sequence database, sequences in the database that represent proteins can be divided into sequences representing the peptides that would result from an actual proteolytic digestion of the proteins. A theoretical spectrum can then be generated for each peptide of a protein represented in the database, based on the sequence of the peptide. The theoretical spectrum includes mass-to-charge peaks that would be expected if the protein in the database were subjected to MS/MS and the peptide of interest was selected for characterization. Each theoretical peptide spectrum for proteins represented in the database can be compared to observed peptide spectra for an unknown protein. The similarity of the theoretical peptide spectra to the unknown peptide spectra can then be used to determine the identity of the unknown protein. The SEQUEST or MASCOT search engines implement such a routine for protein identification. For additional details on such approaches, see Eng J K, McCormack A L, and Yates J R 3rd, *An Approach to Correlate Tandem Mass Spectral Data of Peptides with Amino Acid Sequences in a Protein Database*. J. Am. Soc. Mass. Spectrom. 1994, 5: 976-989, which is hereby incorporated by reference in its entirety.

The matching of proteins based on their MS/MS fragmentation spectra to data from peptides extracted from databases does not necessarily identify them unambiguously or with 100% confidence. Some spectra may match very closely while others match less closely. A close match may or may not indicate the identity of the unknown peptide. The likelihood of observing a close match by chance can be influenced by a variety of aspects of the comparison and search, including the amount of experimental data, size of the database, and redundancy in the database. Ideally, the effects of this variety of aspects are evaluated probabilistically and together, but finding the exact analytical expression can be very difficult.

Simple methods for identifying proteins using peptide match data do not account for most such aspects and so often are unreliable or require ad hoc interpretation. For example, a single peptide match could be used to identify the protein from which it was derived, but this approach may not be reliable. Ranking of matches can be used, but this approach may require ad hoc interpretation. For example, a second-best match in one analysis may be a true match indicating identity, whereas the best match in another analysis may be a false match obtained by chance. A multiplicity of peptide matches can be used to assess the identity of a protein, but this approach can share many of the same biases and shortcomings of other simple methods. Ideally, information indicative of matching is evaluated using methods that are objective, robust, and suitable for automation.

SUMMARY

The invention provides techniques for defining a misidentification probability for an experimental protein divisible into experimental peptides or an experimental peptide.

In general, in one aspect, the invention provides methods and computer programs for defining a misidentification probability for an experimental protein divisible into experimental peptides. The invention receives data representing a set of matches of experimental peptides to reference peptides that can be derived from a protein in a database of proteins; calculates a probability of observing by chance, in a search of the database of proteins, a set of matches equivalent to or better than the represented set of matches; and defines the misidentification probability using the probability of observing by chance a set of matches equivalent to or better than the represented set of matches.

Particular implementations can include one or more of the following features. The probability of observing by chance a set of matches equivalent to or better than the represented set of matches can be expressed as one divided by a number of similar searches of a database of random proteins. The number of similar searches can represent an expected number of similar searches necessary to observe by chance the set of matches equivalent to or better than the represented set of matches. Each similar search can be characterized by an equal expectation that experimental peptides and reference peptides match by chance. Each similar search can be a search for matches of the number of experimental peptides or a greater number of experimental peptides.

The invention can receive data representing an expectation that experimental peptides and reference peptides match by chance, and can calculate the probability of observing by chance a set of matches equivalent to or better than the represented set of matches using the expectation that experimental peptides and reference peptides match by chance. The expectation can be expressed as a ratio of a number of peptides representing a protein in the collection of database proteins to a number of singly counted peptides in the database.

Defining the misidentification probability using the probability of observing by chance a set of matches equivalent to or better than the represented set of matches can include adjusting the probability of observing by chance a set of matches equivalent to or better than the represented set of matches to account for the set of matches including only matches to reference peptides that can be derived from a single protein in the database of proteins. The probability of observing by chance a set of matches equivalent to or better than the represented set of matches can be defined as the upper bound of the misidentification probability.

Each match in the set of matches equivalent to or better than the represented set of matches can be characterized by a likelihood of being observed that is equal to or smaller than a likelihood of observing the set of matches of experimental peptides to reference peptides. For each match in this set of matches, the likelihood of being observed can be defined in whole or in part by a binomial distribution or an approximation of a binomial distribution. The likelihood of being observed can be defined as a function of the form $B(d,n,p) = d!/(n!(d-n)!)p^n(1-p)^{d-n}$, where d is the number of experimental peptides, n is the number of the matches of the subset of the experimental peptides, and p is a measure of the relative size of a protein to a size of the database.

The probability of observing by chance a set of matches equivalent to or better than the represented set of matches can be determined as a function of the form $C(d,n,p) = \Sigma_{i=n}^{d} B(d,i,p) = 1 - \Sigma_{i=0}^{n-1} B(d,i,p)$. $B(d,i,p)$ can be the likelihood of observing i matches of d experimental peptides given a measure p of the relative size of a protein to a size of the database. Defining the misidentification probability using the probability of observing by chance a set of matches equivalent to or better than the represented set of matches can include performing a calculation of the form $D(d,n,p,Q) = 1-(1-C(d,n-1,p))^Q$, where d is the number of experimental peptides, n is the number of the matches of the subset of the experimental peptides, p is a measure of the relative size of a protein to a size of the database, Q is the maximum number of matched proteins, and $C(d, n-1, p)$ is the probability of observing by chance the matches of the number of experimental peptides to reference peptides or better matches of experimental peptides to reference peptides when one experimental peptide is known to match a reference peptide that can be derived from each protein in the collection of Q database proteins.

The expectation that experimental peptides and reference peptides match by chance can be adjusted to account for the effects of small protein databases or very accurate instruments. A calculation of the form $H(d, n, p, \xi, N) = C(d, n, \xi, N) D(d, n, p, Q(d\xi, N))$, where $\xi$ accounts for the effects of small protein databases or very accurate instruments, can be used in the adjustment.

The invention can include receiving data representing additional matches of a number of experimental peptides to reference peptides that can be derived from another protein in a database of proteins; and calculating a probability of observing by chance the additional matches of the number of experimental peptides to reference peptides or better matches of experimental peptides to reference peptides. Defining the misidentification probability using the probability of observing by chance a set of matches equivalent to or better than the represented set of matches can include performing a calculation of the form $E(d, \underline{n}, p, \xi, N) = \min_{i=1...n} [H(id, \Sigma^i_{m=1} n_m, p, \xi, N)]$, where $H(d, n, p, \xi, N) = C(d, n, \xi, N) D(d, n, p, Q(d\xi, N))$ and $\underline{n}$ is a consensus vector including a number of matches of experimental peptides to reference peptides for each of two or more database proteins.

The data representing matches of a number of experimental peptides to reference peptides can include information indicative of the quality of the matches. The data can include correlation values $\Psi$. The correlation values $\Psi$ can be adjusted for the size of the database using the size of a test database, such that $\Psi(S,X) = 1-(1-\Psi_{test}(X))^{S/S_{test}}$. Defining the misidentification probability using the probability of observing by chance a set of matches equivalent to or better than the represented set of matches can include performing a calculation of the form $F(d, \underline{n}, p, \Psi, N) = \min_{k=1...n} E(d, \underline{n}^k, p, \Psi_k, N)$, where $E(d, \underline{n}, p, \Psi, N) = \min_{i=1...n} [H(id, \Sigma^i_{m=1} n_m, p, \Psi, N)]$, $H(d, n, p, \Psi, N) = C(d, n, \Psi, N) D(d, n, p, Q(d \Psi, N))$, and $\underline{n}$ is a consensus vector including a number of matches of experimental peptides to reference peptides for each of two or more database proteins, and $\Psi$ is a vector of values indicating the quality of each of the matches of experimental peptides to reference peptides for each of two or more database proteins.

Calculating a probability of observing by chance the matches of the number of experimental peptides can include correcting for biases introduced by conditions or features of the experimental peptides. Correcting for biases can include using a parameter $\Lambda$. Defining the misidentification probability using the probability of observing by chance a set of matches equivalent to or better than the represented set of matches can include performing a calculation of the form $F(d, \underline{n}, p, \Psi^+, N) = \min_{k=1...n} E(d, \underline{n}^k, p, \Psi_k^+, N)$, where $E(d, \underline{n}, p, \Psi^+, N) = \min_{i=1...n} [H(id, \Sigma^i_{m=1} n_m, p, \Psi^+, N)]$, $H(d, n, p, \Psi^+, N) = C(d, n, \Psi^+, N) D(d, n, p, Q(d \Psi^+, N))$, and $\underline{n}$ is a consensus vector including a number of matches of experimental peptides to reference peptides for each of two or more database proteins, and $\Psi+$ is a vector of values indicating the quality of each of the matches of experimental peptides to reference peptides for each of two or more database proteins and depending upon any of a correlation score, a probability of satisfying other indicia, and effects of small protein databases or very accurate instruments.

The matches of experimental peptides to reference peptides that can be derived from a protein in a database of proteins can be determined by comparing information for the experimental peptides to information for reference peptides that can be derived from a protein in a database of proteins. The information for the experimental peptides can include experimentally determined mass spectra. The information for the reference peptides can include mass spectra determined theoretically from amino acid sequences of the reference peptides.

In general, in another aspect, the invention provides methods and computer programs for defining a peptide misidentification probability for an experimental peptide of a protein divisible into experimental peptides. The invention includes receiving data representing a set of matches of experimental peptides to reference peptides that can be derived from a protein in a database of proteins; calculating a probability of observing by chance, in a search of the database of proteins, a set of matches equivalent to or better than the represented set of matches; defining a protein misidentification probability using the probability of observing by chance a set of matches equivalent to or better than the represented set of matches; and defining the peptide misidentification by adjusting the protein misidentification probability to account for the probability that a peptide is misidentified even if the protein is correctly identified.

Particular implementations can include one or more of the following features. Adjusting the misidentification probability can include determining a probability that the protein is not misidentified and scaling the probability that the protein is not misidentified. Scaling the probability that the protein is not misidentified can include scaling with a probability that at least one of the matches of the number of experimental peptides matches the protein by chance, or scaling with a factor that depends on the number of matches of experimental peptides and a number of experimental peptides expected to be matched.

The invention can include revising the data representing a set of matches of experimental peptides to reference peptides that can be derived from a protein in a database of proteins; calculating a new probability of observing by chance the matches of the number of experimental peptides to reference peptides or better matches of experimental peptides to reference peptides; and defining a new misidentification probability using the new probability of observing by chance a set of matches equivalent to or better than the represented set of matches. The data can be revised by reducing the number of experimental peptides by a number of unambiguously identified experimental peptides.

The invention can be implemented to provide one or more of the following advantages. The use of quantitative information and criteria provides an objective evaluation of the results of protein and peptide identification by searching for matching known peptides. The invention provides a conservative estimate of the probability of obtaining by chance a protein or peptide identification. A probability can be used to assess the reliability of protein or peptide identification based on comparisons of peptide data with theoretically predicted data from known sequences. The methods for estimating a probability are formal and rigorous. The methods for estimating a probability can consider factors such as database size, protein size, number of peptides analyzed, pattern of consensus among proteins and peptides, and correlation values. The probability provides a basis for a confidence assessment of the observed results of a protein match. The methods for calculating and using the probabilities are suitable for use with protein database search engines.

The details of one or more embodiments of the invention are set forth in the accompanying drawings and the description below. Unless otherwise defined, all technical and scientific terms used herein have the meaning commonly understood by one of ordinary skill in the art to which this invention belongs. All publications, patent applications, patents, and other references mentioned herein are incorporated by reference in their entirety. In case of conflict, the present specification, including definitions, will control. Unless otherwise noted, the terms "include", "includes" and "including", and "comprise", "comprises" and "comprising" are used in an open-ended sense—that is, to indicate that the "included" subject matter is a part or component of a larger aggregate or group, without excluding the presence of other parts or components of the aggregate or group. Other features and advantages of the invention will become apparent from the description, the drawings, and the claims.

DESCRIPTION OF DRAWINGS

FIGS. 4A-B are tables illustrating the ranking of peptide matches for experimental peptides, and a consensus report for matching of peptides and proteins to experimental proteins, respectively.

Like reference symbols in the various drawings indicate like elements.

DETAILED DESCRIPTION

The invention provides methods and apparatus, including computer program products, for calculating the confidence of a protein or peptide identification. Proteins are identified by comparing information about peptides of an experimental protein to be identified to information for peptides of proteins in a database, whose identities are typically known. The invention evaluates the confidence or reliability of an identification based on matches of characteristics of one or more peptides of the experimental protein to characteristics of peptides of a database protein, given certain features of the characterization techniques, the database or databases of proteins, and the search.

As used in this specification, a peptide is a polymeric molecule containing two or more amino acids joined by peptide (amide) bonds. A peptide typically is a subunit of a polypeptide or protein, such as a fragment produced by enzymatic cleavage or fragmentation of the parent polypeptide or protein using known techniques. A polypeptide is usually less than 100 amino acids long; one or more polypeptides make a protein. Proteins can be naturally occurring or of a synthetic nature. Naturally occurring proteins can be derived from any source, such as animals (e.g., humans), plants, fungi, bacteria, and/or viruses, and can be obtained for example by sampling cells, tissues, bodily fluids, or elements of the environment such as soil, water, and air. A protein typically can be characterized by its structure and function. However, the methods described in this specification for proteins apply equally to amino acid chains of unknown or unspecified structure and function, as well as aggregates of proteins or protein subunits.

Figure 1:
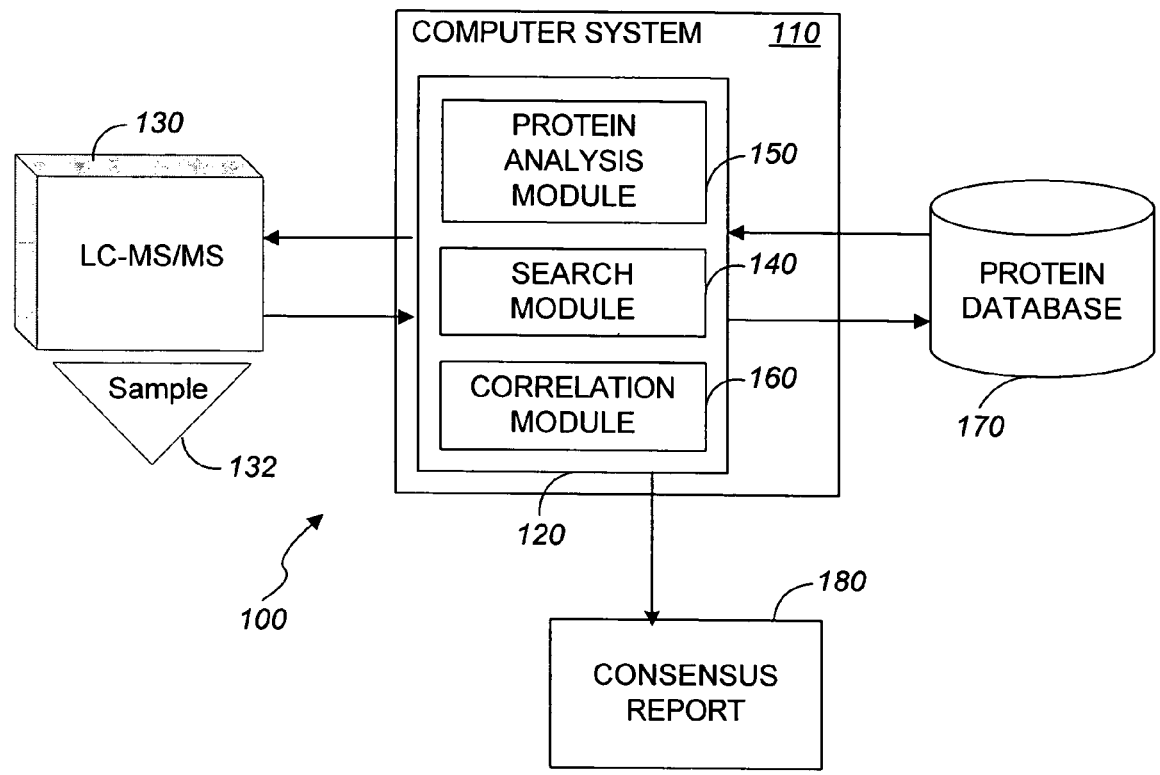
FIG. 1 is a schematic diagram illustrating a system operable to identify proteins according to one aspect of the invention.

FIG. 1 illustrates one implementation of a system 100 for characterizing and identifying proteins according to one aspect of the invention. System 100 includes a general-purpose programmable digital computer system 110 of conventional construction, which can include a memory and one or more processors running an analysis program 120. Computer system 110 has access to a source of data characterizing the peptides of a protein, such as mass spectral data for experimental peptides 130, which in the embodiment shown is a spectrometer capable of performing LC-MS/MS analyses. A source of mass spectral data 130 can be any mass spectrometer capable of generating CID spectra, such as triple quadrupole, ion trap, MALDI-TOF, TOF-TOF, and ICR-FT mass spectrometers. The source of mass spectral data 130 produces mass spectral data for one or more proteins in an experimental sample 132. Computer system 110 also has access to a collection of proteins or protein database 170, such as a public database of amino acid or nucleotide sequence information for proteins. Protein database 170 can be any collection of information for proteins. No particular structure or format of the information in the protein database is required. Computer system 110 outputs data such as a consensus report 180 containing information from comparison of data characterizing the subdivisions of a sample compound or protein such as mass spectral data 130 and comparable data for compounds such as proteins in protein database 170.

System 100 can include input devices, such as a keyboard and/or mouse, and output devices such as a display monitor, as well as conventional communications hardware and software by which computer system 110 can be connected to other computer systems (or to mass analyzer 130 and/or database 170), such as over a network.

Analysis program 120 includes a plurality of computer program modules (some or all of which can alternatively be implemented as separate computer programs), including in one implementation a protein analysis module 150, search module 140, and a correlation module 160. Protein analysis module 150 can take data from a database 170 of proteins and produce information suitable for comparison with information for a experimental protein, such as theoretical peptide spectra. Search module 140 can compare information for a experimental protein with information for proteins derived from protein database 170, and identify those proteins that are similar to the experimental protein. Correlation module 160 can evaluate the similarity between a experimental protein and a protein in database 170.

Figure 2:
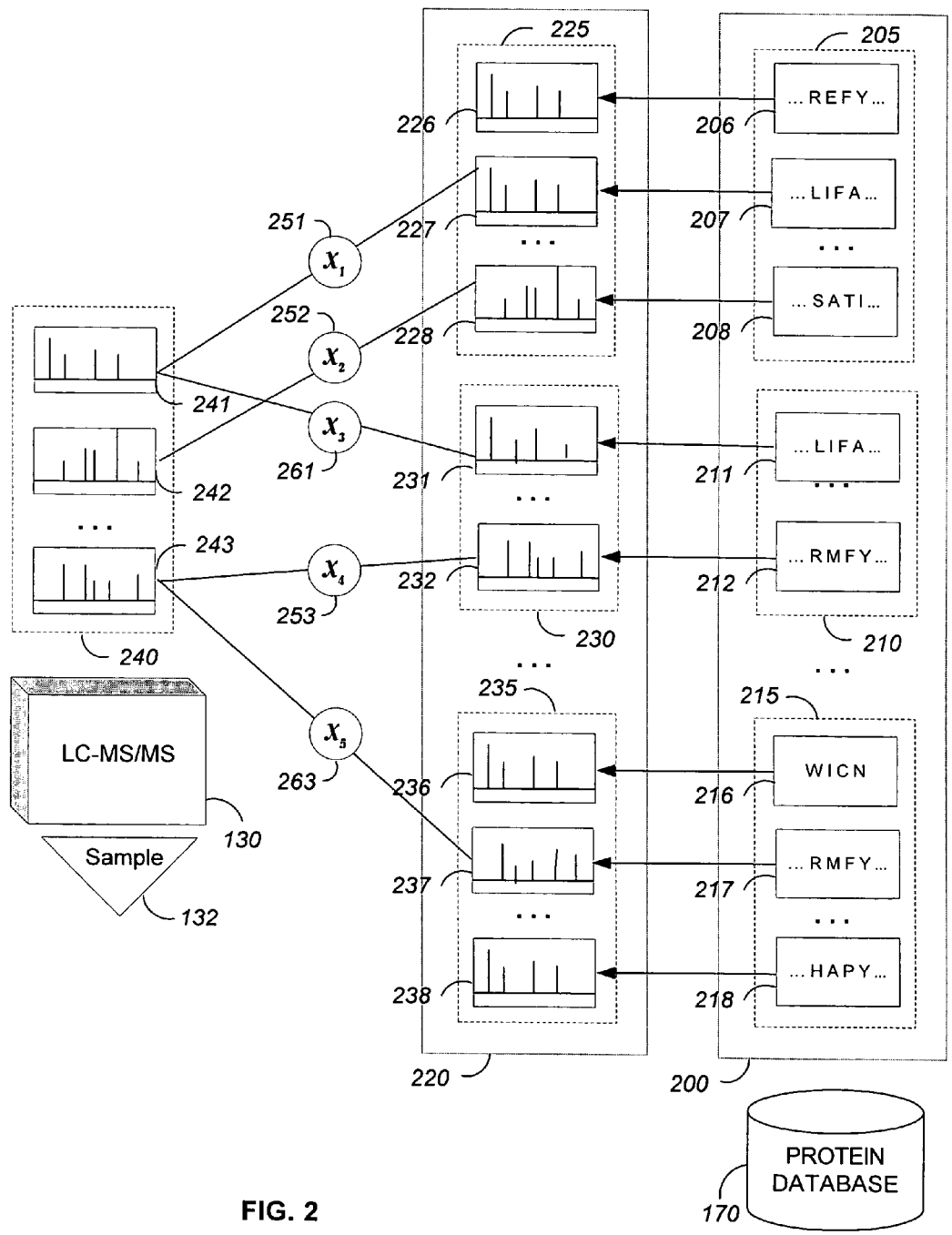
FIG. 2 is schematic diagram illustrating the relationships among protein and peptide information used to identify proteins according to one aspect of the invention.

As shown in FIG. 2, protein database 170 includes one or more sets of protein data 200. A set of protein data 200 includes "actual" data 205, 210, 215 for each of one or more database proteins, such as data from experiments identifying and characterizing the proteins. For example, the actual data can be nucleotide or amino acid sequence data as determined from sequencing of the database proteins by any of several known methods. For each of one or more database proteins, the actual data 205, 210, 215 include information 206-208, 211-212, 216-218 that can be determined to correspond to one or more possible peptides or other possible subdivisions of the database protein, such as the amino acid sequence for a specified peptide. The actual data can include mass spectra for peptides of the database proteins as determined, for example, from the LC-MS/MS analysis of the proteins.

Also as shown in FIG. 2, a source of mass spectral data 130 includes "experimental" data 240 for a protein such as in an experimental sample (the "experimental" protein) 132. The experimental data 240 include information 241, 242, 243 corresponding to one or more peptides or other subdivisions of the experimental protein, such as a peptide spectrum or sequence.

Also as shown in FIG. 2, a second set of data 220 can be derived, either in whole or in part, from the set of protein data 200. The second set of data 220 includes information or "theoretical" data 225, 230, 235 for each of two or more database proteins. The theoretical data 225, 230, 235 are calculated or otherwise determined using actual data 205, 210, 215 for each of one or more database proteins in one or more sets of protein data 200. For example, the theoretical data can be mass spectra that are ascertained using, for example, amino acid sequences and knowledge of the mass and charge properties of the constituent amino acids. For each of two or more database proteins, the theoretical data 225, 230, 235 include information 226-228, 231-232, 236-238 corresponding to one or more peptides or other subdivisions of the protein, such as a peptide spectrum.

The set of actual 200 or theoretical protein data 220 that is used in an analysis of identity can be a subset of the data in the protein database 170 and can represent a subset or collection of the proteins in the protein database. The set of actual 200 or theoretical protein data 220 that is used in an analysis can include data from one or more databases 170.

Information 241, 242, 243 for a peptide from the experimental protein can be used to search the set of actual 200 or theoretical protein data 220, and can be matched to information 227, 231; 228; 232, 237 for peptides of one or more database proteins. For example, information 241 for a peptide of the experimental protein can be matched to information 227 for a peptide of a first database protein and information 231 for a peptide of a second database protein. Also for example, information 242 for a peptide of the experimental protein can be matched to information 228 for a first peptide of a database protein, and information 243 for another peptide of the experimental protein can be matched to information 232 and 236 for a second peptide of the database protein.

Figure 3:
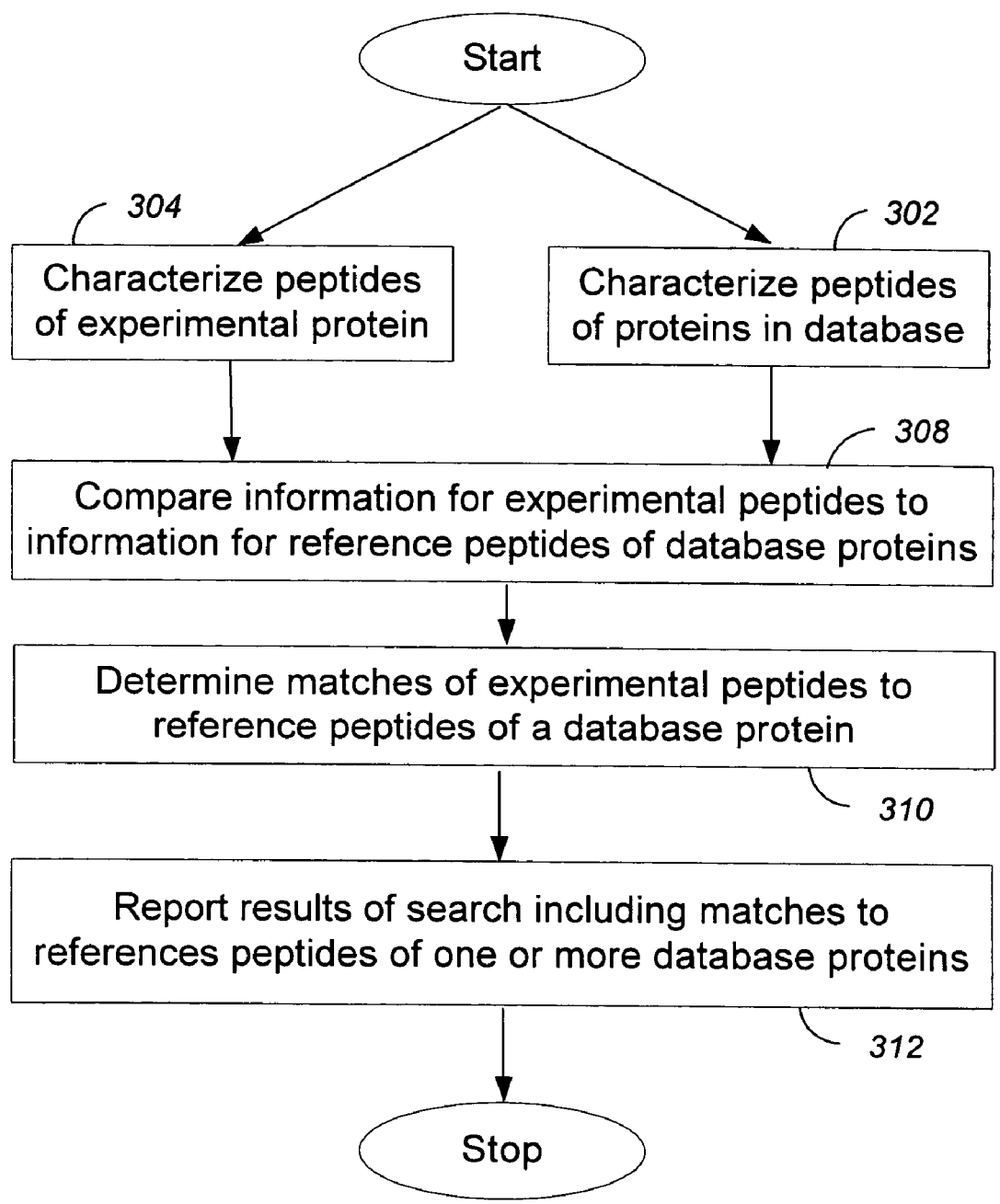
FIG. 3 is a flow chart illustrating a general method for determining the identity of a protein based upon matches of its peptides to information from database proteins.

FIG. 3 is a flow diagram illustrating aspects of a method for comparing experimental proteins to database proteins in order to find a database protein that identifies the experimental protein. The peptides of the proteins in the database must be characterized (step 302); that is, there must be information about the peptides of the proteins in the database suitable for comparison with information about peptides of the experimental protein. For example, the theoretical spectra of peptides from a theoretical digestion of the proteins in the database are determined using sequence information and knowledge such as knowledge of the activity of proteolytic enzymes and the physical characteristics of amino acids, as described above. The peptides of the experimental protein are also characterized (step 304), for example, using LC-MS/MS as described above.

The characteristics of one or more peptides of the experimental protein are then compared to the characteristics of each of one or more peptides of one or more proteins in the database (step 308). For example, the mass spectrum of a peptide from the experimental protein can be compared to mass spectra (theoretical or actual) for peptides of proteins in the database. The quality of the match, e.g. the degree of similarity, can be described, for example, with a correlation score as described in more detail below. Peptide matches are determined for each of one or more proteins in the database (step 310). The matches of experimental peptides to reference peptides that can be derived from one protein in the database of proteins constitutes a set of matches. The results of the comparison include, for each set of matches, characteristics of the matches of the experimental peptides to the reference peptides, such as the number of matches and possibly the quality of each match in the set of matches (step 312).

The comparison of information 241, 242, 243 for an experimental peptide with actual 200 or theoretical data 220 for database proteins can be a multi-step process in which a number of proteins can be pre-selected for further search. For example, a first search can identify information corresponding to one or more peptides having a number of ions (or mass) similar to the number of ions (or mass) for a peptide of the experimental protein. The similarity can be scored, and the scores can be used to identify a set of the actual 200 or theoretical protein data 220 that are possible matches and which warrant further comparison. For example, in FIG. 2, mass information 241, 242, 243 for the peptides of the experimental protein can be used to define a set of potentially matching peptides of database proteins, as shown in FIG. 2 by the connecting lines to information 227, 231; 228; 232, 237 for those peptides.

Information for peptides such as the peptides in the match set can then be compared to information for peptides from the experimental protein using powerful correlation methods such as methods based on the Fourier transform convolution. A figure of merit 251, 252, 261, 253, 263 indicative of the quality of the match of information for a peptide of the experimental protein and information for a peptide of a database protein can be calculated. For example, a correlation coefficient or similarity value such as an X-correlation 251, 252, 261, 253, 263 can be calculated for each match.

For each peptide of the experimental protein, peptides of the database proteins can be ranked according to how well they match the peptide of the experimental protein. For example, for each peptide of the experimental protein, the 10, 15, 50, or 500 best matching peptides from proteins in the potential match set can be listed from best to worst. FIG. 4A shows, for illustrative purposes, a ranking of the two best peptide matches for the example illustrated in FIG. 2. As shown in the table, information 241 for a first peptide of the experimental protein was found to match information 227 for a second peptide of a first protein best and information 231 for a first peptide of a second protein less well but better than any other peptides.

As shown in FIG. 4B, a consensus report summarizes the peptide match information according to proteins in the database 170. For each protein in the database for which information for at least one peptide was found to match information for a peptide of the experimental protein, the consensus report provides results for all peptides of the database protein found to match any peptide of the experimental protein. For each matching peptide, the report provides the X-correlation value as well as the position or rank that the matching peptide has among all the peptides that were found to match the same peptide of the experimental protein.

The matching of peptides may or may not conclusively identify an experimental protein. As illustrated in FIGS. 2 and 3B, two or more proteins may have the same number of peptides matching peptides of the experimental protein. For example, proteins 1 and 2 each have two peptides that match peptides of the experimental protein. Information about the quality of matches may contradict information about the ranking of matches for a peptide of the experimental protein. For example, both peptides of protein 2 match peptides of the experimental protein very well, whereas only one of the two matching peptides of protein 1 matches a peptide of the experimental protein well. In contrast, the rankings of the matches of peptides for protein 1 were higher on average than the rankings of the matches of peptides for protein 2.

Contradictions and difficulties in assessing the correlations or ranks of matches of peptides for an experimental protein with peptides for database proteins, and in inferring the identity of the experimental protein, can be resolved by assessing the probability that the observed results occurred due to chance rather than due to the similar identity of the peptides and proteins. Factors that can affect the probability of a peptide or protein match include the size of the database being searched 170, including the relative number of proteins and peptides; the size of the proteins and peptides or, more generally, the amount of information available for each peptide or protein in the database; the reliability of the information available for each peptide or protein; and the precision of any measure of correlation or similarity of peptides. These factors can have interrelated effects on the probability of a match.

Figure 5:
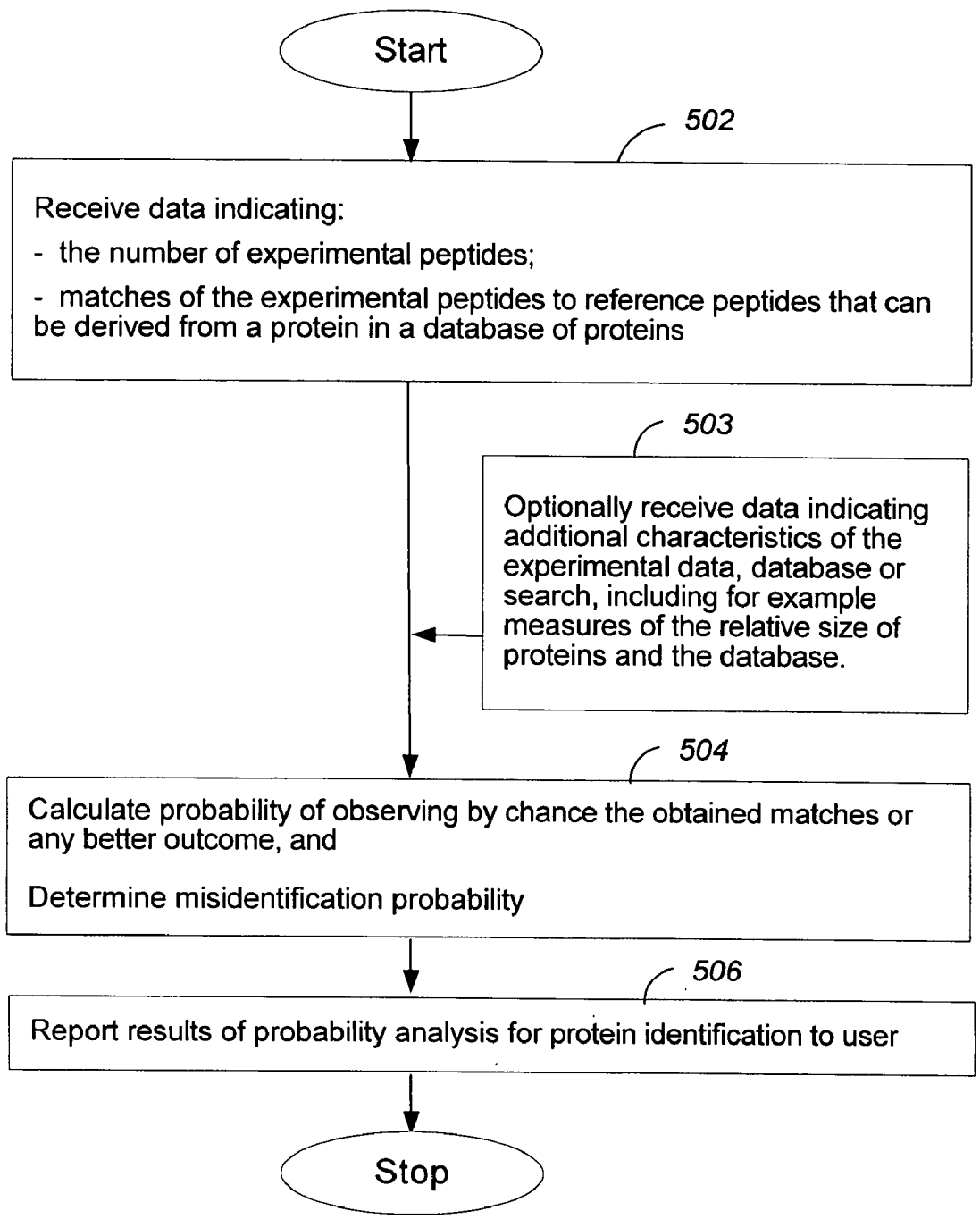
FIG. 5 is a flow chart representing generally a method for evaluating the misidentification probability for an experimental protein identification based upon matches of its peptides to reference peptides that can be derived from a protein in a database of proteins.

FIG. 5 illustrates aspects of a method for evaluating the confidence of an experimental protein identification based upon a set of matches of its peptides to reference peptides that can be derived from a protein in a database of proteins. The method shown receives information indicating characteristics of the set of matches of the experimental peptides to peptides of one or more database proteins, such as the number and possibly quality of matches of experimental peptides to reference peptides that can be derived from a protein in a database of proteins, and a measure of the expectation of matching by chance experimental and reference peptides (step 502). For example, an experimental protein may be divisible into twelve peptides, of which five match well or very well to peptides of protein X in the database of proteins. The method can use the expectation that any of the experimental peptides matches any peptide of proteins in the database, which is typically a number between zero and one. Optionally, the method can receive data indicating additional characteristics of the experimental data, the database of proteins, or the search of the database of proteins (step 503).

The method calculates a probability of observing by chance a set of matches equivalent to or better than the observed set of matches (step 504). The probability of observing the matches by chance is understood in one aspect as the ratio of the number of matches of experimental peptides or any better outcome resulting from a number of similar searches of one or more databases of random proteins to the number of the similar searches. It is one divided by the number of similar searches necessary to observe the matches of the experimental peptides or a better outcome. In this context, two searches are similar if they can be characterized by similar parameters of interest. For example, a similar search can be a search of one or more databases of random sequences having the same number and size of proteins as the actual database. In many cases, a similar search will be a search that has a similar, for example, an equal, expectation that experimental peptides and reference peptides match by chance.

The method also determines a misidentification probability for the match. The calculation of the probability of observing by chance an equivalent or better set of matches or the determination of the misidentification probability can include adjusting the probability of observing the peptide matches to account for the fact that the matches are to reference peptides that can be derived from a single protein in the database of proteins (step 504). In a final step, results for the probability analysis of the experimental protein are reported, for example, to the user (step 506).

Calculating a probability of observing by chance an equivalent or better set of matches and determining a misidentification probability in step 504 can involve the use of several different or related functions and multiple parameters. The functions or parameters for calculating the probability of observing the matches by chance can be specified, for example, by defining a value or referencing an equation, for example, in a search engine or software, or by using a value or an equation in performing calculations according to the described methods.

Figure 6:
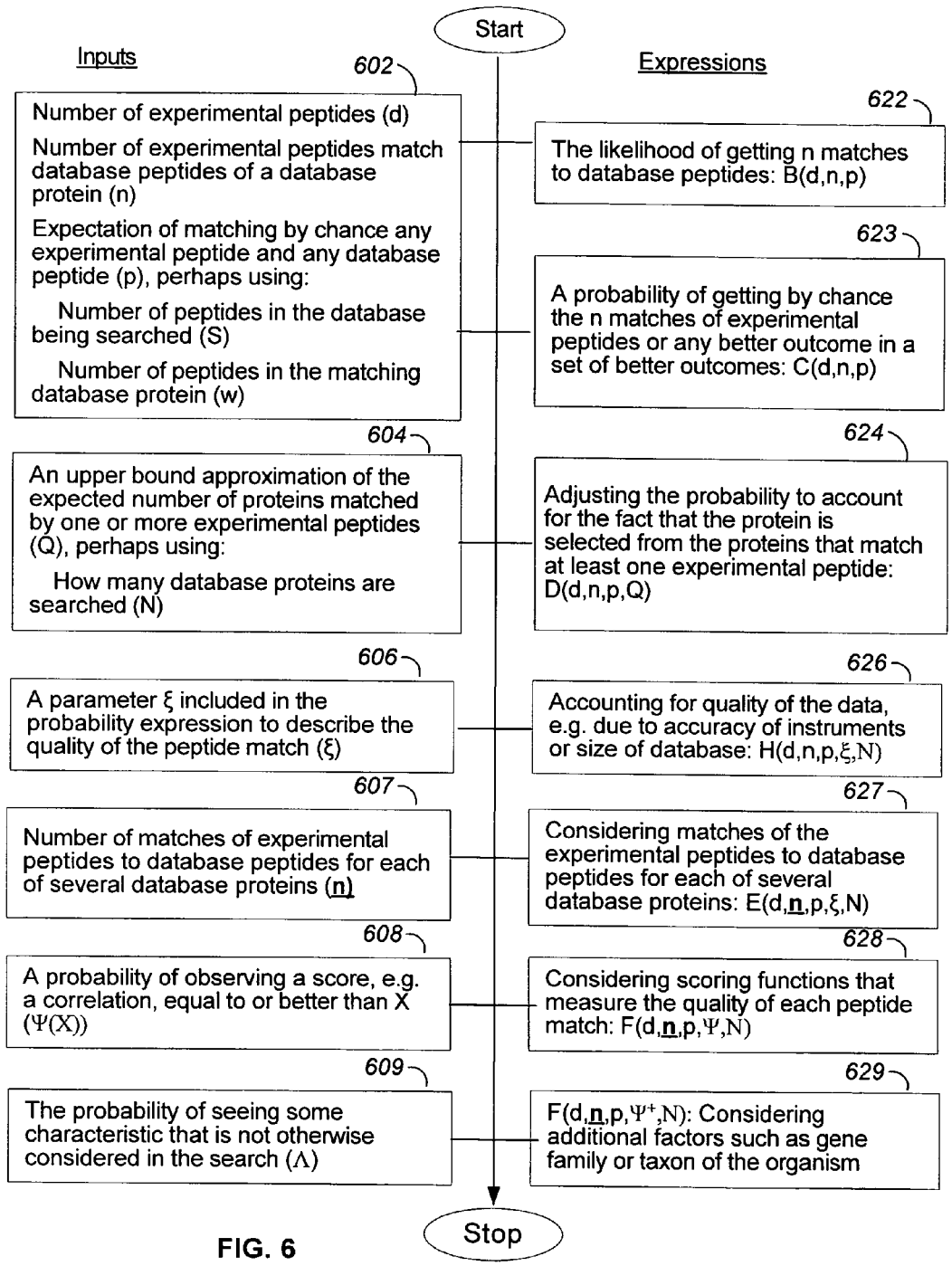
FIG. 6 is a chart describing functions and parameters that can be used in calculating a misidentification probability that observed matches of experimental peptides to reference peptides representing a protein in a database protein indicate the identity of the protein rather than a chance match.

Several possible functions and parameters are described in FIG. 6. The functions and parameters shown are not necessary or sufficient to practice the method, and can be expressed in ways other than those described here. For example, the listed functions can include additional parameters not discussed here, or the listed parameters may be expressed as functions. The listing of these functions and parameters is not intended to limit the scope of the methods, but rather to help summarize and relate the descriptions of the various features of the methods herein as follows.

The step of calculating 504 typically includes the use of one or more expressions or equations 622 defining the likelihood of observing some number of matches to peptides of the database, and one or more expressions or equations 623 defining a probability of getting by chance the specified matches or any better outcome in a set of better outcomes, as shown in FIG. 6. These expressions require certain information 602 regarding a search for reference peptides that match the peptides of an experimental protein, including information about the experimental peptides such as their number (d), information about the experimental peptides that match reference peptides of a database protein such as their number (n), and a measure of the expectation of matching by chance any experimental peptide and any database peptide (e.g. p)—which can depend on other information such as the total number of peptides in the database being searched (S) and the number of peptides in the matching database protein (w).

In one implementation, the likelihood of getting some number of matches to peptides of the database can be defined according to an expression 622 as follows:

$$B(d,n,p)=d!/(n!(d-n)!)p^n(1-p)^{d-n} \quad (1)$$

where d, n, and p are as defined above and in FIG. 6. The function B expresses the probability of matching exactly n peptides. The form of B provided here expresses the probability as a simple binomial distribution in which the n peptide matches are selected from d experimental peptides and p is as described below. Approximations of the binomial or other distributions can be used, and expressions that incorporate or encompass a binomial or other distribution can be used. For example, an expression that includes a binomial distribution or an approximation to a binomial distribution can be used.

The function B relies on a probability parameter or function p. The probability parameter or function describes the expectation of matching by chance experimental and reference peptides—e.g., the probability that a given experimental peptide matches some peptide in a given protein. The parameter p can be approximated as a ratio of the number of different peptides in the matching database protein, w, and the number of different, i.e. singly counted peptides in the database being searched, S, such that p=w/S. The value of the probability, p, can be determined using other expressions or equations. The value of the probability, p, can be estimated, for example with experimental data, as discussed in more detail below.

One example of an expression or equation 623 defining a probability of getting by chance the specified matches or any better outcome in a set of better outcomes is $$C(d,n,p)=\Sigma^d_{i=n}B(d,i,p)=1-\Sigma^{n-1}_{i=0}B(d,i,p) \quad (2)$$

where d, n, and p are as defined above and in FIG. 6. The function C expresses the likelihood or probability of matching n or more peptides—that is, the observed outcome or any possible better outcome. The function C is the sum of the probabilities of matching n peptides, n+1 peptides, n+2 peptides, and so on up to the maximum number of peptides that could be matched, which, in the example here, is the number of peptides in the experimental protein, d. The likelihood of matching any number of peptides greater than n, for example, n+1 peptides, is less than the likelihood of matching n peptides. Thus, the function C describes a probability of observing by chance, as an outcome of a search of the database of proteins, the observed outcome (e.g. the number of matches of experimental peptides to reference peptides) or any better outcome in some set of better outcomes (e.g. any greater number of matches of experimental peptides to database proteins up to the maximum number of experimental peptides), where the likelihood of each of the better outcomes is less than the likelihood of the observed outcome.

The step of calculating 504 also typically includes the use of one or more expressions or equations 624, as shown in FIG. 6, that adjust the probability of the observed or better matches to account for the fact that the protein is any protein of the database, not a particular one—that is, the protein is not selected before the search, but rather after the search is performed. We are interested in knowing the probability to have n or more matches in some protein, not any particular protein. (The calculation to have a particular protein match n or more times is described by the function C.) The expression or equation 624 depends, directly or indirectly, on a figure or function (Q) 604 that describes an upper bound approximation of the expected number of proteins matched by one or more experimental peptides, which we refer to here as the maximum number of matched proteins. The quantity Q can be determined as a function of the number of database proteins that are searched. The quantity Q can be defined, for example, as Q(d,n)=max(1,min(d,N)), where d is the number of experimental peptides and N is the number of proteins represented by the peptides being searched. Q(d,n) represents an upper bound to the maximum number of proteins that can be matched with at least one peptide One example of an expression or equation 624 adjusting the probability of the observed or better matches to account for the fact that the matches are to reference peptides that can be derived from any single protein in the database of proteins is:

$$D(d,n,p,Q)=1-(1-C(d,n-1,p))^Q \quad (3)$$

where d, n, p, and Q are as defined above and in FIG. 6. The function D 624 incorporates the features of function C, upon which it relies. But unlike function C, function D describes the probability that n or more peptides of the experimental protein are matched to peptides of any database protein, considering the number of database proteins expected to have at least one matching peptide.

The function D 624 can be understood as follows. The probability that n or more peptides of some (any) protein are matched is equal to the probability of not having any of the Q proteins (proteins matched at least once) matched by n or more peptides, that is $1-(1-C(d,n-1,p))^Q$. The function D can use a classical expression for the conditional probability. For example, D can be defined as $1-(1-(C(d,n,p)/C(d,1,p)))^N$.

The exact form of the functions B, C, and D 622, 623, 624 and their constituent expressions and parameters can vary, as will be apparent to one of skill in the art. The functions can, for example, encompass additional parameters or variables such as the number of peptides being searched, the relative number of peptides and proteins, or the number of proteins in the database. The functions can be extended, for example, to consider the quality of the data or search 626, matches to multiple database proteins 627, the quality of matches 628, or additional features 629, as described in more detail below. All of the equations, parameters, and variables discussed herein are merely exemplary, and are provided to explain and illustrate the principles and features of the techniques described.

The step of calculating 504 can include, as shown in FIG. 6, the use of one or more expressions or equations 626 that include a parameter 606 accounting for the quality of the matches. For example, expressions or equations 626 can include a parameter ξ in the probability expressions or calculations to consider the quality of the peptide match. The parameter can be included to consider the accuracy of the peptide precursor mass, for example, when the instrument is very accurate or when the database is small. It can be extended, as described below with reference to Λ to account for other aspects of the match quality, such as correlation scores. When used to account for peptide precursor accuracy, parameter $\xi$ can be defined, for example, as $1-\gamma^S$, where $\gamma$ is a positive constant less than one and S is the number of peptides being searched. The value of $\gamma$ can depend on a variety of features of the technology, methodology, and analysis, including features of the mass spectrometer used to identify the mass of the peptides of the experimental protein, the digestion used to create the peptides of the experimental protein, the calculations used to derive the masses of the peptides of the database proteins, and the methods used to compare and equate the masses. The value of $\gamma$ can be calculated statistically as the $1/S_{test}$ power of the proportion of the peptides in a test database of size $S_{test}$ that do not match a test peptide.

One example of an expression or equation 626 accounting for the quality of the comparisons is $$H(d,n,p,\xi,N)=C(d,n,\xi)D(d,n,p,Q(d\xi,N)). \tag{5}$$

where d, n, p, $\xi$, and N are as defined above and in FIG. 6. This expression for H has two independent factors, the first accounting for the match quality and the second accounting for the fact that those matches are in the same protein. The factor Q is modified to reflect the fact that a lower number of matched proteins could be expected. For example, Q can be defined as max (1, min ($d\xi$, N)).

The calculations 504 can include one or more expressions or equations 627 that consider matches of the experimental peptides to reference peptides for each of two or more reference peptides, as shown in FIG. 6. These expressions require information 607 about the matches of experimental peptides to reference peptides for each of several database proteins, for example, a consensus vector n (boldface n)—represented here as $\underline{\mathbf{n}}$ (boldface and underline) to distinguish it more clearly from n—that lists the number of matches of experimental peptides to each of the several reference peptides. The database proteins having peptides that match the experimental peptides are each referred to here as an "option" for the identification of the experimental protein. A consensus vector provides, for each option, the number of peptides from the option protein that match peptides of the experimental protein. For example, a consensus vector, $\underline{\mathbf{n}}=(n_1, n_2, \ldots n_J)$, means that an experimental protein matches $n_1$ peptides of a first protein or option, $n_2$ peptides of a second protein or option, and so on.

One example of an expression or equation 627 that considers matches to multiple database proteins, i.e. multiple options for identification, defines the probability of observing by chance a consensus vector equal to or better than the observed consensus vector as follows:

$$E(d,n,p,\xi,N)=\min_{i=1\ldots J}[H(i,d,\Sigma^i_{m=1}n_m,p,\xi,N)] \tag{6}$$

where d, $\underline{\mathbf{n}}$, p, $\xi$, and N are as defined above and in FIG. 6. The function E can incorporate the features of function H, as shown here, using $\xi$ as described above. The function E is based upon the probabilistic equivalence between having two matches for each experimental peptide and having twice the number of experimental peptides.

The calculations 504 can include one or more expressions or equations 628, as shown in FIG. 6, that consider scores measuring the quality of each peptide match. These expressions require certain information 608 describing the probability of observing a particular score or any better score. The quality of the match between a peptide of the experimental protein and a peptide of a database protein can be measured, for example, by a correlation score, X, which occurs with some probability $\phi(X)$. The probability of observing a correlation equal to or better than X is then $\Psi(X)=\int\phi(u)du$.

Adjustments to the probability distribution $\phi(X)$ and the function $\Psi(X)$ are possible. For example, the probability $\Psi(X)$ can depend on the size of the database, S, such that $\Psi(X)=1-\alpha(X)^S$ for some function $\alpha(X)$. If a function, $\Psi_{test}$ (X), for a database of length $S_{test}$, is known or can be estimated, the equation for $\Psi(X)$ can be adjusted for the size of the database such that $\Psi(S,X)=1-(1-\Psi_{test}(X))^{S/S}$test. The distribution of X-values may depend on peptide charge or peptide size, although the correlations are often normalized in such a way that they are independent of the charge state and size of the peptides. The distribution of X-values expected by chance can be estimated by searching for peptides of an experimental protein of known identity in a database that does not contain that protein, or in a random database One example of an expression or equation 628 that considers a scoring function $\Psi(X)=\int\phi(u)du$, is $$F(d,\underline{n},p,\xi,N)=\min_{k=1\ldots n}E(d,\underline{n}^k,p,\Psi_k,N), \tag{7}$$

where d, $\underline{\mathbf{n}}$, p, $\Psi$, and N are as defined above and in FIG. 6. The features of function E can be incorporated as shown here in equation F. In addition, the function E depends on a new set of parameters, $\Psi_k$, which provides the scores for the k best peptide matches. To determine $\Psi_k$, the $\Psi$ values for all the matching peptides of each protein option represented in $\underline{\mathbf{n}}$ are arranged from lowest (the best value) to highest (the worst value) to define a vector such as $\Psi_n=(\Psi_1, \Psi_2, \Psi_3, \ldots \Psi_k, \Psi_{k+1}, \Psi_{k+2}, \ldots \Psi_n)$, where each $\Psi_i$ represents the correlation for a peptide i, matching a peptide of a given protein of the database. This group of peptides is then truncated to include only the k best matching peptides, where, if there are n potentially matching peptides, $1 \leq k \leq n$ and $\Psi_k=(\Psi_1, \Psi_2, \Psi_3, \ldots \Psi_k)$. The function E also adjusts the consensus vector to be a restriction vector, $\underline{\mathbf{n}}^k$, that includes only the peptides that are represented in $\Psi_k$, the truncated set of the k best matching peptides. For example, if there are eight matching peptides for a first protein option, such that $n_1=8$, but only 5 of those peptides have $\Psi$ values among the k best $\Psi$ values, then the value for the first protein option is revised such that $n_1^k=5$. Similarly, if there are 7 matching peptides for a second protein option, such that that $n_2=7$, but only 6 of those peptides have $\Psi$ values among the k best $\Psi$ values, then the value for the second protein option is revised such that $n_1^k=6$. Thus, both $\Psi_k$ and the restriction vector have k components; that is, $\Sigma^n_{i=1}n_i^k=k$. The function F is then defined as the minimum value of the function E. That is, the function F ranges over all possible number of best peptide matches (values of k), identifies the number having the smallest possible value of $E(d, \underline{n}^k, p, \Psi_k, N)$, and defines F as for that number of best peptide matches.

The calculations 504 also can include, as shown in FIG. 6, one or more expressions or equations 629 considering additional factors or "independent indicia"—such as a gene family or organismal taxon—that affect the probability of observing a correlation equal to or better than X. These expressions require certain information 609 describing the probability of seeing some characteristic that is not otherwise considered in the search. For example, a function $\Psi^+$ can describe the likelihood of observing a peptide match with a correlation of X, a probability $\Lambda$ of satisfying other indicia, which are independent of the X-scoring process, and a probability of a peptide match $\xi$, as $\Psi^+(\Psi,\xi,\Lambda)=\xi\Lambda\Psi$.

The use of the factor $\Lambda$ can correct for biases due to expected features of the matched peptide sequence(s) that may not be true for all the proteins or peptides in the database.

For example, if a protein has been digested with trypsin but the sequences being searched are not limited to those that are compatible with trypsin, there is a bias. The bias can be corrected, for example, by setting $\Lambda=(2/20)^2\times(1-2/20)^{q-1}$. This $\Lambda$ describes the probability of having a matching tryptic peptide, which is the product of the probability that the matching peptide has trypsin cleavable residues, namely lysine or arginine, at one site and does not have lysine or arginine at any of q−1 remaining sites. The expression assumes that the probability of having a trypsin cleavable residue at any location in a peptide is 2/20, so that the probability that the peptide has lysine or arginine at the end and before the peptide is $(2/20)^2$ while the probability that remaining amino acids (q−1) do not have any R or K is $(1-2/20)^{q-1}$. Analogous corrections can be made for other digestive enzymes.

Corrections of biases introduced by other conditions or features of the comparison are possible. For example, if the experimental protein is a mouse protein but the sequences being searched are not limited to mouse proteins, there is a bias. The bias can be corrected by setting $\Lambda=(n_{mouse}/n_{total})$, where $n_{mouse}$ is the number of mouse proteins in the database and $n_{total}$ is the total number of peptides in the database. Products of multiple independent factors are possible as well.

One example of an expression or equation 629 that considers independent indicia such as described above is $$F(d,\underline{n},p,\Psi^+,N)=\min_{k=1\ldots n}E(d,\underline{n}^k,p,\Psi_k^+,N), \quad (8)$$

where the parameters are as defined previously for function F except that $\Psi$ is replaced with $\Psi^+$ as defined above and the restrictions of the vector $n^k$ are done now according to the $\Psi^+$ value instead of the $\Psi$ value.

The expressions shown in FIG. 6 and described above provide the basis for assessing a protein or peptide identification. The misidentification probability, $MP_{proteins}(X)$, estimates the probability that the observed set of peptide matches, or a better set, happens by chance. For example, a misidentification probability of one in one million means that, if the experiment is repeated one million times, an identification as good as the observed identification, or better, is expected to happen by chance only one time.

For example, the misidentification probability, MP, can be upper bounded by the function, $D(d,n,p,Q)$ such that $MP_{protein} \leq D(d,n,p,Q)$ and $P\sim 1-D(d,n,p,Q)$. Similarly, a misidentification probability, MP, can be upper bounded by the functions, $H(d,n,p,\xi,N)$, $E(d,\underline{n},p,\xi,N)$, $F(d,\underline{n},p,\Psi,N)$, or $F(d,\underline{n},p,\Psi^+,N)$. It has been found experimentally that these methods above often discriminate with several orders of magnitude difference between correct and incorrectly matched proteins.

Misidentification probabilities for peptides, $MP_{peptides}$ and $MP^*_{peptides}$, can be defined as a function of the probability p, defined above, the number of peptides being searched (d), and the misidentification probabilities for proteins, $MP_{protein}=D(d,n,p,Q)$, as follows:

$$MP_{peptide}=MP_{protein}+(1-MP_{protein})F, \text{ where } F=(1-(1-p)^d) \quad (9)$$

$$MP^*_{peptide}=MP_{protein}+(1-MP_{protein})F, \text{ where } F=(dp/\max(dp,n)) \quad (10)$$

Each of these peptide misidentification probabilities is a sum of the probability that the protein is misidentified and a second quantity, which is a fraction F of the probability that the protein is not misidentified, $(1-MP_{protein})$. The second quantity can be understood as the probability that a peptide is misidentified even if the protein from which the peptide was derived was correctly identified.

In general, $MP_{peptide}$ measures the likelihood of having some (any) incorrect peptide match, while $MP^*_{peptide}$ measures the likelihood that a particular peptide is incorrectly identified. The first misidentification probability, $MP_{protein}$, scales the second quantity by $1-(1-p)^d$, which is the probability that at least one of the d experimental peptides matches the protein by chance. This factor is based on the probability that a peptide does not match, $1-p$, and the probability that none of the d peptides being searched matches, which is $(1-p)^d$.

The second misidentification probability, $MP^*_{peptides}$, scales the second quantity by $(dp/\max(dp,n))$, which is a factor that depends on how many peptides were matched and how many were expected to be matched. For a search of d peptides and a probability, p, that an experimental peptide will match one of the peptides of the protein where the match is observed, the expected number of chance peptide matches for that protein is dp. If the number, n, of peptides of a protein that are matched is smaller than the expected number of chance matches, n<dp, then a protein is not reliably identified by the matches. In this case, $F=dp/dp=1$ and the second quantity is simply $(1-MP_{protein})$, such that $MP^*_{peptides}=1$, which means that the outcome could be by chance.

If the number, n, of peptides of a protein that are matched is larger than the expected number of chance matches, n>dp, then a protein could be reliably identified. That is, if n>dp, $MP^*_{protein}\approx 0$, in which case $F=dp/n$, and $MP^*_{peptide}\rightarrow dp/\max(dp,n)$, or equivalently, $$nMP^*_{peptide}\rightarrow dp, \quad (11)$$

which indicates that the sum of the misidentification probabilities for the matched peptides of a protein approaches the expected number of chance matches as the protein misidentification probability goes to zero. For example, if a protein is correctly identified with 10 peptide matches such that n>dp, and dp=1, then $MP^*_{peptide}\approx dp/n=1/10$. Thus, the second probability MP* is defined as a measure of expected ratio of misidentified peptides in the proteins and should fulfill the relation $$I \equiv \sum_{\forall z} MP^*_{peptide}(z), \quad (12)$$

where I is the total number of expected incorrectly assigned peptides when the sum runs over all the peptide assignations in all the proteins.

The misidentification probabilities $MP_{peptides}$ and $MP^*_{peptides}$ can be extended to account for searches of a small database using $\xi$ and the misidentification probabilities for proteins, $MP_{protein}=H(d,n,p,\xi)$, as follows:

$$MP_{peptide}=MP_{protein}+(1-MP_{protein})F, \text{ where } F=(1-(1-p\xi)^d)$$

$$MP^*_{peptide}=MP_{protein}+(1-MP_{protein})F, \text{ where } F=A(d,p,\xi,n)=(dp\xi/\max(dp\xi,n))$$

The misidentification probability $MP_{peptides}$ and $MP^*_{peptides}$ can be defined for use with a consensus vector using b and the misidentification probabilities for proteins, $MP_{protein}=E(d,n,p,\xi,N)$, as follows:

$MP_{peptide}=MP_{protein}+(1-MP_{protein})F$, where $F=(1-p\xi)^{bd})$ $MP^*_{peptide}=MP_{protein}+(1-MP_{protein})F$, where $F=G(b,d,p,\xi,\underline{n})=\min_{i=b\ldots}\, {}_fA(d,p,\xi,n)$ The parameter b characterizes the rank of the peptide match that is of interest. For example, if the peptide match evaluated had the protein as its best $4^{th}$ protein candidate, then b=4. To take into account the effect of the previously discussed independent indicia factors, the values of $\Psi^+$ can be used to rank the peptides.

The misidentification probability $MP_{peptides}$ and $MP^*_{peptides}$ can be defined to take into account the correlation score, or X-values, and the misidentification probabilities for proteins, $MP_{protein}=F(d,\underline{n},p,\Psi^+,N)$, as follows:

$MP_{peptide}=MP_{protein}+(1-MP_{protein})F$, where $F=(1-(1-p\Psi_a^+)^{bd})$ $MP^*_{peptide}=MP_{protein}+(1-MP_{protein})F$, where $F=J(b,a,d,p,\underline{n},\Psi^+)=\min_{k=a\ldots n}G(b,d,p,\Psi_k^+,n^k)$ The parameter a characterizes, for the peptide of interest, the rank of the peptide match in a protein. For example, if the peptide match evaluated is in a protein that has said peptide match as its best $5^{th}$ matching peptide, then a=5.

The equations above are all conservative estimates of the misidentification probability. Each tends to overestimate the misidentification probability rather than underestimating it, so as not to permit misidentifications to be interpreted as reliable identifications.

The techniques described above can be used in an iterative way to improve the sensitivity of the probability estimation and help avoid false negatives. In general, in an iterative model, the misidentification probabilities for a search of d peptides are calculated using any of the methods discussed above. One or more parameters are adjusted based upon the calculated misidentification probabilities, and the misidentification probabilities are re-calculated using the adjusted parameters. The process can be repeated until a specified aspect of the calculations, such as a resulting decision as to the correctness of each protein identification, remains constant with consecutive iterations.

In one aspect of an iterative model, the number of peptides being searched, d, can be adjusted to remove from consideration peptides that are characterized by low misidentification probabilities, and hence are reliably or unambiguously identified. A count, x, of the peptides having low misidentification probabilities can be used to redefine d as d'=d−x. The probabilities for the ambiguously identified proteins are then recalculated using d'. For example, for a search of the spectra for 13 peptides, each of which has 2 possible charge states, the number of peptides being searched is d=2(13)=26. If two proteins are matched, one with n=10 peptide assignations and a very low misidentification probability, and the other with n=3 peptides and a high misidentification probability, then x=2(10) and the probabilities for the second protein can be recalculated using d'=d−x=26−2(10)=6.

The techniques described herein can be used to evaluate the reliability of results of an actual search for peptides of an experimental protein. For example, a search engine can search information representing peptides associated with database proteins for spectra corresponding to the spectra of peptides derived from the experimental protein. A number of peptides associated with a particular protein represented in the database can be identified as matching the peptides of the experimental protein. The misidentification probability can be calculated for the features of the search, using methods such as those described above. The techniques described herein also can be used to evaluate the reliability of potential results of a search of information representing peptides associated with database proteins. For example, the techniques can be used to evaluate the probability of observing any number of matches of peptides in a hypothetical search of the database. The techniques can be used, for example, to determine how many matches of peptides would be required to have confidence that the matches indicate the identity of a hypothetical experimental protein.

Aspects of the invention can be implemented in digital electronic circuitry, or in computer hardware, firmware, software, or in combinations of them. Some or all aspects of the invention can be implemented as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Some or all of the method steps of the invention can be performed by one or more programmable processors executing a computer program to perform functions of the invention by operating on input data and generating output. Method steps can also be performed by, and apparatus of the invention can be implemented as, special purpose logic circuitry, e.g., an FPGA (field programmable gate array) or an ASIC (application-specific integrated circuit). The methods of the invention can be implemented as a combination of steps performed automatically, under computer control, and steps performed manually by a human user, such as a scientist.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices; magnetic disks, e.g., internal hard disks or removable disks; magneto-optical disks; and CD-ROM and DVD-ROM disks. The processor and the memory can be supplemented by, or incorporated in special purpose logic circuitry.

To provide for interaction with a user, the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well.

A number of embodiments of the invention have been described. Nevertheless, it will be understood that various modifications may be made without departing from the spirit and scope of the invention. For example, the methods described herein apply to any method of comparison of peptides of proteins, including any method of amino acid and nucleotide sequence comparison. Accordingly, other embodiments are within the scope of the following claims.

What is claimed is:

1. A method for defining a misidentification probability, comprising:

dividing an experimental protein into one or more experimental peptides using a liquid chromatography (LC) tandem mass spectrometer (MS/MS);

providing MS/MS data of the one or more experimental peptides by way of the liquid chromatography (LC) tandem mass spectrometer (MS/MS);

receiving data representing a set of matches of the one or more experimental peptides to reference peptides that can be derived from a protein in a database of proteins;

calculating a probability of observing by chance, in a search of the database of proteins, a set of matches equivalent to or better than the represented set of matches, wherein the probability of observing by chance a set of matches equivalent to or better than the represented set of matches can be expressed as one divided by a number of similar searches of a database of random proteins, the number of similar searches representing an expected number of similar searches necessary to observe by chance the set of matches equivalent to or better than the represented set of matches;

defining the misidentification probability using the probability of observing by chance a set of matches equivalent to or better than the represented set of matches, wherein the step of defining the misidentification probability includes performing a calculation of the form $$D(d,n,p,Q) = 1-(1-C(d,n-1,p))^Q$$

where d is the number of experimental peptides, n is the number of the matches of a subset of the experimental peptides, a parameter p being a measure of the relative size of a database protein to a size of the database, wherein the measure of the relative size is approximated as a ratio of the number of different peptides in the matching database protein, w, and a number of different singly counted peptides in the database being searched, S, such that p=w/S, Q is a maximum number of matched proteins, wherein Q is defined as $Q(d,n)=\max(1,\min(d,N))$, where d is the number of experimental peptides and N is the number of proteins represented by the peptides being searched so that Q(d,n) represents an upper bound to the maximum number of proteins that can be matched with at least one peptide, and C(d, n−1, p) is the probability of observing by chance the matches of the number of experimental peptides to reference peptides or better matches of experimental peptides to reference peptides when one experimental peptide is known to match a reference peptide that can be derived from each protein in the collection of database proteins; and outputting to a user, the results of the probability analysis of the experimental protein, wherein the misidentification probability indicates to the user the likelihood of having an incorrect peptide match.

2. The method of claim 1, further comprising:

receiving data representing an expectation that experimental peptides and reference peptides match by chance;

wherein calculating the probability of observing by chance a set of matches equivalent to or better than the represented set of matches includes calculating using the expectation that experimental peptides and reference peptides match by chance.

3. The method of claim 1, wherein:

each similar search is characterized by an equal expectation that experimental peptides and reference peptides match by chance.

4. The method of either claim 2 or claim 3, wherein:

the expectation that experimental peptides and reference peptides match by chance can be expressed as a ratio of a number of peptides representing a protein in the collection of database proteins to a number of singly counted peptides in the database.

5. The method of claim 1, wherein:

defining the misidentification probability using the probability of observing by chance a set of matches equivalent to or better than the represented set of matches includes adjusting the probability of observing by chance a set of matches equivalent to or better than the represented set of matches to account for the set of matches being a set of matches to reference peptides that can be derived from any single protein.

6. The method of claim 1, wherein:

defining the misidentification probability using the probability of observing by chance a set of matches equivalent to or better than the represented set of matches includes defining the probability of observing by chance a set of matches equivalent to or better than the represented set of matches as the upper bound of the misidentification probability.

7. The method of claim 1, wherein:

each match in the set of matches equivalent to or better than the represented set of matches is characterized by a likelihood of being observed that is equal to or smaller than a likelihood of observing the set of matches of experimental peptides to reference peptides.

8. The method of claim 7, wherein:

for each match in the set of matches equivalent to or better than the represented set of matches, the likelihood of being observed is defined in whole or in part by a binomial distribution or an approximation of a binomial distribution.

9. The method of claim 7, wherein:

for each match in the set of matches equivalent to or better than the represented set of matches, the likelihood of being observed is determined as a function of the form:

$$B(d,n,p) = d!/(n!(d-n)!)p^n(1-p)^{d-n}$$

where d is the number of experimental peptides, n is the number of the matches of a subset of the experimental peptides, the parameter p being a measure of the relative size of a database protein to a size of the database, wherein the measure of the relative size is approximated as a ratio of the number of different peptides in the matching database protein, w, and a number of different singly counted peptides in the database being searched, S, such that p=w/S.

10. The method of claim 9, wherein:

the probability of observing by chance a set of matches equivalent to or better than the represented set of matches is determined as a function of the form:

$$C(d,n,p) = \Sigma^d_{i=n} B(d,i,p) = 1 - \Sigma^{n-1}_{i=0} B(d,i,p).$$

11. The method of claim 10, wherein:
defining the misidentification probability using the probability of observing by chance a set of matches equivalent to or better than the represented set of matches includes adjusting the probability of observing by chance a set of matches equivalent to or better than the represented set of matches to account for the set of matches equivalent to or better than the represented set of matches including only matches to reference peptides that can be derived from any single protein.

12. The method of claim 11, wherein:
adjusting the probability to account for the set of matches equivalent to or better than the represented set of matches including only matches to reference peptides that can be derived from a single protein in the database of proteins includes defining a maximum number of matched proteins, the maximum number of matched proteins being an upper bound approximation of the expected number of proteins matched by one or more experimental peptides.

13. The method of claim 1, wherein:

$$C(d,n,p)=\Sigma^d_{i=n}B(d,i,p)=1-\Sigma^{n-1}_{i=0}B(d,i,p)$$

where $B(d,i,p)$ is the likelihood of observing i matches of d experimental peptides given the parameter p, wherein the parameter p further describes the expectation of matching by chance experimental and reference peptides.

14. The method of claim 13, wherein:

$$B(d,n,p)=d!/(n!(d-n)!)p^n(1-p)^{d-n}.$$

15. The method of claim 2, wherein:
the expectation that experimental peptides and reference peptides match by chance is adjusted to account for the effects of small protein databases or very accurate instruments.

16. The method of one of claims 13-14, wherein:
defining the misidentification probability using the probability of observing by chance a set of matches equivalent to or better than the represented set of matches includes performing a calculation of the form $$H(d,n,p,\xi,N)=C(d,n,\xi)D(d,n,p,Q(d\xi,N))$$

where $\xi$ accounts for the effects of small protein databases or very accurate instruments.

17. The method of claim 1, further comprising:
receiving data representing additional matches of a number of experimental peptides to reference peptides that can be derived from another protein in a database of proteins; and
calculating a probability of observing by chance the additional matches of the number of experimental peptides to reference peptides or better matches of experimental peptides to reference peptides.

18. The method of one of claims 13-14, wherein:
defining the misidentification probability using the probability of observing by chance a set of matches equivalent to or better than the represented set of matches includes performing a calculation of the form $$E(d,\underline{n},p,\xi,N)=\min_{i=1\ldots f}[H(id,\Sigma^i_{m=1}n_m,p,\xi,N]$$

where $$H(d,n,p,\xi,N)=C(d,n,\xi,N)D(d,n,p,Q(d\xi,N))$$

and $\underline{n}$ is a consensus vector including a number of matches of experimental peptides to reference peptides for each of two or more database proteins.

19. The method of claim 1, wherein:
data representing matches of a number of experimental peptides to reference peptides includes information indicative of the quality of the matches.

20. The method of claim 19, wherein:
data representing matches of a number of experimental peptides to reference peptides includes correlation values $\Psi$.

21. The method of claim 20, wherein:
the correlation values $\Psi$ are adjusted for the size of the database using the size of a test database, such that $$\Psi(S,X)=1-(1-\Psi_{test}(X))^{S/Stest}.$$

22. The method of one of claims 13-14, wherein:

$$F(d,\underline{n},p,\Psi,N)=\min_{k=1\ldots n}E(d,\underline{n}^k,p,\Psi_k,N),$$

where $$E(d,\underline{n},p,\Psi,N)=\min_{i=1\ldots f}[H(id,\Sigma^i_{m=1}n_m,p,\Psi,N],$$

$$H(d,n,p,\Psi,N)=C(d,n,\Psi,N)D(d,n,p,Q(d\Psi,N)),$$

and $\underline{n}$ is a consensus vector including a number of matches of experimental peptides to reference peptides for each of two or more database proteins, and $\Psi$ is a vector of values indicating the quality of each of the matches of experimental peptides to reference peptides for each of two or more database proteins.

23. The method of claim 1, wherein:
calculating a probability of observing by chance the matches of the number of experimental peptides includes correcting for biases introduced by conditions or features of the experimental peptides.

24. The method of claim 23, wherein:
correcting for biases introduced by conditions or features of the experimental peptides includes using a parameter $\Lambda$.

25. The method of one of claims 13-14, wherein:

$$F(d,\underline{n},p,\Psi^+,N)=\min_{k=1\ldots n}E(d,\underline{n}^k,p,\Psi_k^+,N),$$

where $$E(d,\underline{n},p,\Psi^+,N)=\min_{i=1\ldots f}[H(id,\Sigma^i_{m=1}n_m,p,\Psi^+,N],$$

$$H(d,n,p,\Psi^+,N)=C(d,n,\Psi^+,N)D(d,n,p,Q(d\Psi^+,N)),$$

and $\underline{n}$ is a consensus vector including a number of matches of experimental peptides to reference peptides for each of two or more database proteins, and $\Psi^+$ is a vector of values indicating the quality of each of the matches of experimental peptides to reference peptides for each of two or more database proteins and depending upon any of a correlation score, a probability of satisfying other indicia, and effects of small protein databases or very accurate instruments.

26. A method for defining a peptide misidentification probability, the method comprising:
dividing an experimental protein into one or more experimental peptides using a liquid chromatography (LC) tandem mass spectrometer (MS/MS);
providing MS/MS data of the one or more experimental peptides by way of the liquid chromatography (LC) tandem mass spectrometer (MS/MS);
receiving data representing a set of matches of experimental peptides to reference peptides that can be derived from a protein in a database of proteins;

calculating a probability of observing by chance, in a search of the database of proteins, a set of matches equivalent to or better than the represented set of matches;

defining a protein misidentification probability using the probability of observing by chance a set of matches equivalent to or better than the represented set of matches, which includes performing a calculation of the form $$D(d,n,p,Q)=1-(1-C(d,n-1,p))^Q$$

where d is the number of experimental peptides, n is the number of the matches of a subset of the experimental peptides, a parameter p being a measure of the relative size of a database protein to a size of the database, wherein the measure of the relative size is approximated as a ratio of the number of different peptides in the matching database protein, w, and a number of different singly counted peptides in the database being searched, S, such that p=w/S, Q is a maximum number of matched proteins, wherein Q is defined as Q(d,n)=max(1,min(d,N)), where d is the number of experimental peptides and N is the number of proteins represented by the peptides being searched so that Q(d,n) represents an upper bound to the maximum number of proteins that can be matched with at least one peptide, and C(d, n−1, p) is the probability of observing by chance the matches of the number of experimental peptides to reference peptides or better matches of experimental peptides to reference peptides when one experimental peptide is known to match a reference peptide that can be derived from each protein in the collection of database proteins;

defining the peptide misidentification by adjusting the protein misidentification probability to account for the probability that a peptide is misidentified even if the protein is correctly identified; and outputting to a user, the results of the probability analysis of the experimental protein, wherein the adjusted misidentification probability indicates to the user the likelihood of having an incorrect peptide match even if the protein is correctly identified.

27. The method of claim 26, wherein:

adjusting the misidentification probability includes determining a probability that the protein is not misidentified and scaling the probability that the protein is not misidentified.

28. The method of claim 27, wherein:

scaling the probability that the protein is not misidentified, includes scaling with a probability that at least one of the matches of the number of experimental peptides matches the protein by chance.

29. The method of claim 28, wherein:

scaling the probability that the protein is not misidentified includes scaling with a factor that depends on the number of matches of experimental peptides and a number of experimental peptides expected to be matched.

30. The method of claim 19, further comprising:

revising data representing a set of matches of experimental peptides to reference peptides that can be derived from a protein in a database of proteins;

calculating a new probability of observing by chance the matches of the number of experimental peptides to reference peptides or better matches of experimental peptides to reference peptides; and defining a new misidentification probability using the new probability of observing by chance a set of matches equivalent to or better than the represented set of matches; and outputting the misidentification probability to a user.

31. The method of claim 30, wherein:

revising data representing a set of matches of experimental peptides to reference peptides that can be derived from a protein in a database of proteins includes reducing the number of experimental peptides by a number of unambiguously identified experimental peptides.

32. The method of claim 1, wherein:

the matches of experimental peptides to reference peptides that can be derived from a protein in a database of proteins are determined by comparing information for the experimental peptides to information for reference peptides that can be derived from a protein in a database of proteins.

33. The method of claim 32, wherein:

the information for the experimental peptides includes experimentally determined mass spectra.

34. The method of claim 32, wherein:

the information for the reference peptides includes mass spectra determined theoretically from amino acid sequences of the reference peptides.

35. A computer program on a machine-readable storage device for defining a misidentification probability for an experimental protein divisible into experimental peptides, the computer program comprising computer executable instructions to:

receive data representing a set of matches of experimental peptides to reference peptides that can be derived from a protein in a database of proteins;

calculate a probability of observing by chance, in a search of the database of proteins, a set of matches equivalent to or better than the represented set of matches, wherein the probability of observing by chance a set of matches equivalent to or better than the represented set of matches can be expressed as one divided by a number of similar searches of a database of random proteins, the number of similar searches representing an expected number of similar searches necessary to observe by chance the set of matches equivalent to or better than the represented set of matches;

define the misidentification probability using the probability of observing by chance a set of matches equivalent to or better than the represented set of matches, which includes instructions to perform a calculation of the form $$D(d,n,p,Q)=1-(1-C(d,n-1,p))^Q$$

where d is the number of experimental peptides, n is the number of the matches of a subset of the experimental peptides, a parameter p being a measure of the relative size of a database protein to a size of the database, wherein the measure of the relative size is approximated as a ratio of the number of different peptides in the matching database protein, w, and a number of different singly counted peptides in the database being searched, S, such that p=w/S, Q is a maximum number of matched proteins, wherein Q is defined as Q(d,n)=max(1,min(d, N)), where d is the number of experimental peptides and N is the number of proteins represented by the peptides being searched so that Q(d,n) represents an upper bound to the maximum number of proteins that can be matched with at least one peptide, and C(d, n−1, p) is the probability of observing by chance the matches of the number of experimental peptides to reference peptides or better matches of experimental peptides to reference peptides when one experimental peptide is known to match a reference peptide that can be derived from each protein in the collection of database proteins; and outputting the misidentification probability to a user.

36. The computer program of claim 35, further comprising computer executable instructions to:

receive data representing an expectation that experimental peptides and reference peptides match by chance;

wherein instructions to calculate the probability of observing by chance a set of matches equivalent to or better than the represented set of matches include instructions to calculate using the expectation that experimental peptides and reference peptides match by chance.

37. The computer program of claim 35, wherein:

each similar search is characterized by an equal expectation that experimental peptides and reference peptides match by chance.

38. The computer program of either claim 36 or claim 37, wherein:

the expectation that experimental peptides and reference peptides match by chance can be expressed as a ratio of a number of peptides representing a protein in the collection of database proteins to a number of singly counted peptides in the database.

39. The computer program of claim 35, wherein:

the computer executable instructions to define the misidentification probability using the probability of observing by chance a set of matches equivalent to or better than the represented set of matches include computer executable instructions to adjust the probability of observing by chance a set of matches equivalent to or better than the represented set of matches to account for the set of matches being a set of matches to reference peptides that can be derived from any single protein.

40. The computer program of claim 35, wherein:

the computer executable instructions to define the misidentification probability using the probability of observing by chance a set of matches equivalent to or better than the represented set of matches include computer executable instructions to define the probability of observing by chance a set of matches equivalent to or better than the represented set of matches as the upper bound of the misidentification probability.

41. The computer program of claim 35, wherein:

each match in the set of matches equivalent to or better than the represented set of matches is characterized by a likelihood of being observed that is equal to or smaller than a likelihood of observing the set of matches of experimental peptides to reference peptides.

42. The computer program of claim 41, wherein:

for each match in the set of matches equivalent to or better than the represented set of matches, the likelihood of being observed is defined in whole or in part by a binomial distribution or an approximation of a binomial distribution.

43. The computer program of claim 41, wherein:

for each match in the set of matches equivalent to or better than the represented set of matches, the likelihood of being observed is determined as a function of the form:

$$B(d,n,p)=d!/(n!(d-n)!)p^n(1-p)^{d-n}$$

where d is the number of experimental peptides, n is the number of the matches of a subset of the experimental peptides, and the parameter p being a measure of the relative size of a database protein to a size of the database, wherein the measure of the relative size is approximated as a ratio of the number of different peptides in the matching database protein, w, and a number of different singly counted peptides in the database being searched, S, such that p=w/S.

44. The computer program of claim 43, wherein:

the probability of observing by chance a set of matches equivalent to or better than the represented set of matches is determined as a function of the form:

$$C(d,n,p)=\Sigma^d_{i=n}B(d,i,p)=1-\Sigma^{n-1}_{i=0}B(d,i,p).$$

45. The computer program of claim 44, wherein:

the computer executable instructions to define the misidentification probability using the probability of observing by chance a set of matches equivalent to or better than the represented set of matches include computer executable instructions to adjust the probability of observing by chance a set of matches equivalent to or better than the represented set of matches to account for the set of matches equivalent to or better than the represented set of matches including only matches to reference peptides that can be derived from any single protein.

46. The computer program of claim 45, wherein:

the computer executable instructions to adjust the probability to account for the set of matches equivalent to or better than the represented set of matches including only matches to reference peptides that can be derived from a single protein in the database of proteins include computer executable instructions to define a maximum number of matched proteins, the maximum number of matched proteins being an upper bound approximation of the expected number of proteins matched by one or more experimental peptides.

47. The computer program of claim 35, wherein:

$$C(d,n,p)=\Sigma^d_{i=n}B(d,i,p)=1-\Sigma^{n-1}_{i=0}B(d,i,p)$$

where B(d,i,p) is the likelihood of observing i matches of d experimental peptides given the parameter p, wherein the parameter p further describes the expectation of matching by chance experimental and reference peptides.

48. The computer program of claim 47, wherein:

$$B(d,n,p)=d!/(n!(d-n)!)p^n(1-p)^{d-n}.$$

49. The computer program of claim 36, wherein:

the expectation that experimental peptides and reference peptides match by chance is adjusted to account for the effects of small protein databases or very accurate instruments.

50. The computer program of one of claims 47-48, wherein:

instructions to define the misidentification probability using the probability of observing by chance a set of matches equivalent to or better than the represented set of matches includes performing a calculation of the form $$H(d,n,p,\xi,N)=C(d,n,\xi,N)D(d,n,p,Q(d\xi,N)$$

where $\xi$ accounts for the effects of small protein databases or very accurate instruments.

51. The computer program of claim 35, further comprising computer executable instructions to:

receive data representing additional matches of a number of experimental peptides to reference peptides that can be derived from another protein in a database of proteins;

calculate a probability of observing by chance the additional matches of the number of experimental peptides to reference peptides or better matches of experimental peptides to reference peptides; and outputting the misidentification probability to a user.

52. The computer program of one of claims 47-48, wherein:

the computer executable instructions to define the misidentification probability using the probability of observing by chance a set of matches equivalent to or better than the represented set of matches include computer executable instructions to perform a calculation of the form $$E(d,\underline{n},p,\xi,N)=\min_{i=1\ldots r} f[H(id,\Sigma^i_{m=1}n_m,p,\xi,N]$$

where $$H(d,n,p,\xi,N)=C(d,n,\xi,N)D(d,n,p,Q(d\xi,N))$$

and $\underline{n}$ is a consensus vector including a number of matches of experimental peptides to reference peptides for each of two or more database proteins.

53. The computer program of claim 35, wherein:

data representing matches of a number of experimental peptides to reference peptides includes information indicative of the quality of the matches.

54. The computer program of claim 53, wherein:

data representing matches of a number of experimental peptides to reference peptides includes correlation values $\Psi$.

55. The computer program of claim 54, wherein:

the correlation values $\Psi$ are adjusted for the size of the database using the size of a test database, such that $$\Psi(S,X)=1-(1-\Psi_{test}(X))^{S/Stest}.$$

56. The computer program of one of claims 47-48, wherein:

$$F(d,\underline{n},p,\Psi,N)=\min_{k=1\ldots r} E(d,\underline{n}_k,p,\Psi_k,N),$$

where $$E(d,\underline{n},p,\Psi,N)=\min_{i=1\ldots r} f[H(id,\Sigma^i_{m=1}n_m,p,\Psi,N],$$

$$H(d,n,p,\Psi,N)=C(d,n,\Psi,N)D(d,n,p,Q(d\Psi,N)),$$

and $\underline{n}$ is a consensus vector including a number of matches of experimental peptides to reference peptides for each of two or more database proteins, and $\Psi$ is a vector of values indicating the quality of each of the matches of experimental peptides to reference peptides for each of two or more database proteins.

57. The computer program of claim 35, wherein:

the computer executable instructions to calculate a probability of observing by chance the matches of the number of experimental peptides include computer executable instructions to correct for biases introduced by conditions or features of the experimental peptides.

58. The computer program of claim 57, wherein:

the computer executable instructions to correct for biases introduced by conditions or features of the experimental peptides include computer executable instructions for using a parameter $\Lambda$.

59. The computer program of one of claims 47-48, wherein:

$$F(d,\underline{n},p,\Psi^+,N)=\min_{k=1\ldots r} E(d,\underline{n}^k,p,\Psi_k^+,N),$$

where $$E(d,\underline{n},p,\Psi^+,N)=\min_{i=1\ldots r} f[H(id,\Sigma^i_{m=1}n_m,p,\Psi^+,N],$$

$$H(d,n,p,\Psi^+,N)=C(d,n,\Psi^+,N)D(d,n,p,Q(d\Psi^+,N)),$$

and $\underline{n}$ is a consensus vector including a number of matches of experimental peptides to reference peptides for each of two or more database proteins, and $\Psi^+$ is a vector of values indicating the quality of each of the matches of experimental peptides to reference peptides for each of two or more database proteins and depending upon any of a correlation score, a probability of satisfying other indicia, and effects of small protein databases or very accurate instruments.

60. A computer program on a machine-readable storage device for defining a peptide misidentification probability for an experimental peptide of a protein divisible into experimental peptides, the computer program comprising computer executable instructions to:

receive data representing a set of matches of experimental peptides to reference peptides that can be derived from a protein in a database of proteins;

calculate a probability of observing by chance, in a search of the database of proteins, a set of matches equivalent to or better than the represented set of matches;

define a protein misidentification probability using the probability of observing by chance a set of matches equivalent to or better than the represented set of matches, which includes a calculation of the form $$D(d,n,p,Q)=1-(1-C(d,n-1,p))^Q$$

where d is the number of experimental peptides, n is the number of the matches of a subset of the experimental peptides, a parameter p being a measure of the relative size of a database protein to a size of the database, wherein the measure of the relative size is approximated as a ratio of the number of different peptides in the matching database protein, w, and a number of different singly counted peptides in the database being searched, S, such that p=w/S, Q is a maximum number of matched proteins, wherein Q is defined as Q(d,n)=max(1,min(d, N)), where d is the number of experimental peptides and N is the number of proteins represented by the peptides being searched so that Q(d,n) represents an upper bound to the maximum number of proteins that can be matched with at least one peptide, and C(d, n−1, p) is the probability of observing by chance the matches of the number of experimental peptides to reference peptides or better matches of experimental peptides to reference peptides when one experimental peptide is known to match a reference peptide that can be derived from each protein in the collection of database proteins;

define the peptide misidentification by adjusting the protein misidentification probability to account for the probability that a peptide is misidentified even if the protein is correctly identified; and outputting the misidentification probability to a user.

61. The computer program of claim 60, wherein:

the computer executable instructions to adjust the misidentification probability include computer executable instructions to determine a probability that the protein is not misidentified and scale the probability that the protein is not misidentified.

62. The computer program of claim 61, wherein:

the computer executable instructions to scale the probability that the protein is not misidentified, include computer executable instructions to scale with a probability that at least one of the matches of the number of experimental peptides matches the protein by chance.

63. The computer program of claim 62, wherein:

the computer executable instructions to scale the probability that the protein is not misidentified include computer executable instructions to scale with a factor that depends on the number of matches of experimental peptides and a number of experimental peptides expected to be matched.

64. The computer program of claim 53, further comprising computer executable instructions to:
revise data representing a set of matches of experimental peptides to reference peptides that can be derived from a protein in a database of proteins;
calculate a new probability of observing by chance the matches of the number of experimental peptides to reference peptides or better matches of experimental peptides to reference peptides;
define a new misidentification probability using the new probability of observing by chance a set of matches equivalent to or better than the represented set of matches; and
outputting the misidentification probability to a user.

65. The computer program of claim 64, wherein:
the computer executable instructions to revise data representing a set of matches of experimental peptides to reference peptides that can be derived from a protein in a database of proteins include computer executable instructions to reduce the number of experimental peptides by a number of unambiguously identified experimental peptides.

66. The computer program of claim 35, wherein:
the matches of experimental peptides to reference peptides that can be derived from a protein in a database of proteins are determined by comparing information for the experimental peptides to information for reference peptides that can be derived from a protein in a database of proteins.

67. The computer program of claim 66, wherein:
the information for the experimental peptides includes experimentally determined mass spectra.

68. The computer program of claim 66, wherein:
the information for the reference peptides includes mass spectra determined theoretically from amino acid sequences of the reference peptides.

* * * * *

UNITED STATES PATENT AND TRADEMARK OFFICE
CERTIFICATE OF CORRECTION

PATENT NO. : 7,593,817 B2
APPLICATION NO. : 10/738667
DATED : September 22, 2009
INVENTOR(S) : Fernando M. Maroto It is certified that error appears in the above-identified patent and that said Letters Patent is hereby corrected as shown below:

Claim 59, Column 27, line 65:

replace "$E(d, n, p, .+, N) = \min i=1..f [ H(id, \Sigma im=1 \, nm, p, \psi+, N]$,"

with --$E(d, n, p, \psi+, N) = \min i=1..f [ H(id, \Sigma im=1 \, nm, p, \psi+, N]$,--

Signed and Sealed this

Twelfth Day of January, 2010

David J. Kappos
*Director of the United States Patent and Trademark Office*